United States Patent [19]

Kristiansen

[11] Patent Number: 4,891,362
[45] Date of Patent: Jan. 2, 1990

[54] SUBSTITUTED AMIDOPHOSPHONATES AND AMIDOPHOSPHATES

[75] Inventor: Odd Kristiansen, Möhlin, Switzerland

[73] Assignee: Ciba-Geigy Corporation, Ardsley, N.Y.

[21] Appl. No.: 212,392

[22] Filed: Jun. 27, 1988

[30] Foreign Application Priority Data

Jul. 8, 1987 [CH] Switzerland .................. 02585/87
May 6, 1988 [CH] Switzerland .................. 01732/88

[51] Int. Cl.⁴ .................. A01N 57/02; A01N 57/08; C07F 9/24; C07F 9/36
[52] U.S. Cl. .................. 514/90; 514/129; 544/63; 558/177
[58] Field of Search .......... 558/177; 544/63; 514/90, 129

[56] References Cited

U.S. PATENT DOCUMENTS 3,773,801 11/1973 Hofer et al. .................. 558/177
4,036,956 7/1977 Stolzer et al. ................ 514/129
4,071,533 1/1978 Stein et al. .................. 260/332.5
4,386,082 5/1983 Arlt et al. .................... 558/177 X

FOREIGN PATENT DOCUMENTS 3316891 11/1984 Fed. Rep. of Germany .

OTHER PUBLICATIONS

Derwent Abstract of JP 87,045,876; J8 7045—876-B.

Hamer, Journal of the Chemical Society (1965), pp. 2731-2736.

Primary Examiner—Richard L. Raymond
Attorney, Agent, or Firm—Kevin T. Mansfield; Edward McC. Roberts

[57] ABSTRACT

Novel substituted N-alkyl-N-alkoxyamidophosphonates or -thiophosphonates and N-alkyl-N-alkoxyamidophosphates or -thiophosphates of formula

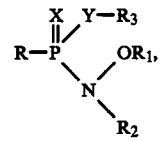

wherein
R is $C_1$–$C_4$ alkyl or $C_1$–$C_4$ alkoxy,
$R_1$ and $R_3$ are each independently of the other $C_1$–$C_4$ alkyl,
$R_2$ is hydrogen, $C_4$–$C_4$ alkyl, or when taken together with $R_1$, forms the radical —$(CH_2)_4$—; and
X and Y are each independently of the other oxygen or sulfur, with the proviso that at least one of X or Y is sulfur if $R_2$ is hydrogen.

The preparation of these compounds is described, as well as the use thereof in pest control, especially for controlling insects and representatives of the order Acarina.

15 Claims, No Drawings

SUBSTITUTED AMIDOPHOSPHONATES AND AMIDOPHOSPHATES

The present invention relates to novel substituted N-alkyl-N-alkoxyamidophosphonates or -thiophosphonates and to N-alkyl-N-alkoxyamidophosphates or -thiophosphates, to the preparation of these compounds and to the use thereof in pest control.

The compounds of this invention have the formula I

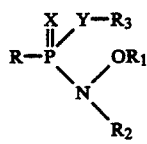

wherein
R is $C_1$–$C_4$alkyl or $C_1$–$C_4$alkoxy,
$R_1$ and $R_3$ are each independently of the other $C_1$–$C_4$alkyl,
$R_2$ is hydrogen, $C_1$–$C_4$alkyl, or when taken together with $R_1$, forms the radical —$(CH_2)_4$—; and
X and Y are each independently of the other oxygen or sulfur, with the proviso that at least one of X or Y is sulfur if $R_2$ is hydrogen.

The alkyl or alkoxy groups may be straight chain or branched. Examples of such groups are: methyl, methoxy, ethyl, ethoxy, n-propyl, isopropyl, n-butyl, isobutyl, sec-butyl and tert-butyl.

Preferred compounds of formula I are those wherein
R is $C_1$–$C_4$alkyl or $C_1$–$C_4$alkoxy,
$R_1$, $R_2$ and $R_3$ are each independently $C_1$–$C_4$alkyl, or $R_1$ and $R_2$, when taken together, form the radical —$(CH_2)_4$—; and
X and Y are each independently of the other oxygen or sulfur.

Further preferred compounds of formula I are those wherein
R is $C_1$–$C_4$alkyl,
$R_1$ and $R_2$ are each methyl or, when taken together, form the radical —$(CH_2)_4$—,
$R_3$ is $C_3$–$C_4$alkyl;
X is oxygen or sulfur, and
Y is sulfur.

Particularly preferred compounds of formula I are those wherein R is methyl or ethyl.

To be singled out for special mention on account of their biological activity are compounds of formula I, wherein X and Y are sulfur.

Compounds of formula I which also merit special mention are those wherein $R_3$ is n-propyl, isopropyl, sec-butyl or tert-butyl.

The compounds of formula I can be prepared in a manner known per se by reacting a compound of formula II

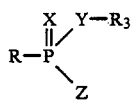

with a compound of formula III

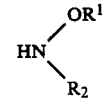

in which formulae the substituents R, $R_1$, $R_2$, $R_3$, X and Y have the meanings previously assigned to them and Z is halogen, preferably chlorine.

The above process is preferably carried out in the presence of an inert solvent or diluent and at least one equivalent of an acid acceptor or base. Particularly suitable acid acceptors or bases are tertiary amines such as trialkylamines and pyridine, and also hydrides, hydroxides, oxides and carbonates of alkali metals and alkaline earth metals, as well as alkali metal alcoholates, for example potassium tert-butylate and sodium methylate and the like. Depending on the nature of the solvent employed, the reaction temperature is normally in the range from −5° to +140° C., preferably from 0° to 70° C.

It is preferred to carry the above process out under normal or elevated pressure. Examples of suitable solvents or diluents are ether and ethereal compounds such as diethyl ether, diisopropyl ether, dioxane, 1,2-dimethoxyethane and tetrahydrofuran; amides such as N,N-dialkylated carboxamides; aliphatic, aromatic and halogenated hydrocarbons such as benzene, toluene, xylenes, chloroform, methylene chloride and chlorobenzene; as well as dimethyl sulfoxide.

The starting N,O-dialkylhydroxylamines of formula III are known and readily obtainable. The phosphonyl halides of formula II are also known or, if novel, can be obtained by methods analogous to known ones (q.v. for example U.S. Pat. No. 4 428 945, 4 473 562, 4 535 077, and European patent 0 025 270). In that case they likewise consitute an object of this invention.

It is already known from Japanese patent 87-045 876 that N-alkylamidothiophosphonates have insecticidal and miticidal activity. N-Alkylamidothiophosphonates and N-alkylsulfonylamidothiophosphonates are disclosed as pesticides in U.S. Pat. No. 4 390 529 and European patent application 0 241 098, respectively. N-Formylamidothiophosphonates having insecticidal, miticidal and nematicidal properties are disclosed in U.S. Pat. No. 4 683 224 and in European patent applications 164 308 and 215 509. The compounds of formula I of this invention differ substantially in structure from these prior art compounds in that they contain an alkoxy-substituted amido group. N-Alkoxyamidophosphates and N-alkoxyamidophosphonates having synergistic herbicidal activity have also been disclosed in German Offenlegungsschrift 3 316 891. However, these compounds differ in structure from the compounds of this invention in that they contain a 2,2,2-trihaloethylphosphate or -phosphonate group.

Surprisingly, it has been found that the compounds of formula I are suitable for controlling a variety of pests of animals and plants as well as soil pests. The compounds of formula I can thus be used for controlling insects, for example of the orders: Lepidoptera, Coleoptera, Homoptera, heteroptera, Diptera, Thysanoptera, Orthoptera, Anoplura, Siphonaptera, Mallophaga, Thysanura, Isoptera, Psocoptera and Hymenoptera and mites and ticks of the order Acarina.

The compounds of formula I are suitable for controlling plant-destructive insects in ornamentals and crops of useful plants, in particular in cotton crops (e.g. Spodoptera littoralis and Heliothis virescens). The compounds of formula I are particularly effective against soil insects (e.g. *Aulacophora femoralis, Chortophila brassicae, Diabrotica balteata, Pachnoda savignyi* and *Scotia ypsilon*). The compounds of formula I are also very effective against larval insect stages and nymphs, especially of noxious feeding insects. The compounds of formula I can also be used very successfully for controlling plant-destructive cicadas, especially in rice crops.

The compounds of formula I are also effective against plant-destructive acarids (spider mites, for example of the families Tetranychidae, Tarsonemidae, Eriophydae, Tyroglyphidae and glycyphagidae) and also against ectoparasitic acarids (mites and ticks, for example of the families Ixodidae, Argasidae, Sarcoptidae and Dermanyssidae) that infest productive livestock.

The pesticidal activity of the compounds of this invention can be substantially broadened and adapted to prevailing circumstances by addition of other insecticides and/or acaricides. Examples of suitable additives include: organophosphorus compounds, nitrophenols and derivatives thereof, formamidines, ureas, pyrethroids and also carbamates and chlorinated hydrocarbons.

The good pesticidal activity of the compounds of formula I of the invention corresponds to a mortality of at least 50-60% of the above pests.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; silicone oils or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g.

polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in "McCutcheon's Detergents and Emulsifiers Annual", MC Publishing Corp., Ridgewood, N.J. 1979; Dr. Helmut Stache, "Tensid Taschenbush" (Handbook of Surfactants), Carl Hanser Verlag, Munich/Vienna, 1981.

The pesticidal compositions usually contain 0.1 to 99%, preferably 0.1 to 95%, of a compound of formula I, 1 to 99.9% of a solid or liquid adjuvant, and 0 to 25%, preferably 0.1 to 25%, of a surfactant. The percentages are by weight.

Whereas commercial products are preferably formulated as concentrates, the end user will normally employ diluted formulations of substantially lower concentration, for example 0.1 to 1000 ppm.

The compositions may also contain further ingredients, such as stabilisers, antifoams, viscosity regulators, binders, tackifiers as well as fertilisers or other active ingredients for obtaining special effects.

EXAMPLE 1

Preparation of N-methyl-N-methoxy-S-sec-butyl ethylamidodithiophosphonate

A mixture of 1.41 g of N,O-dimethylhydroxylamine and 2.34 g of triethylamine is added dropwise to a solution of 5 g of S-sec-butyl ethyldithiophosphonyl chloride in 20 ml of methylene chloride. The mixture is stirred for 1 hour at room temperature and then heated under reflux for 8 hours. After cooling, the reaction mixture is extracted with 20 ml of water. The separated organic phase is dried over sodium sulfate, concentrated by evaporation, and the crude product is purified by column chromatography ($SiO_2$ with a 1:1 mixture of hexane/methylene chloride as eluant), affording the title compound of formula

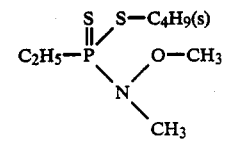

as a colourless liquid with a refractive index of $n_D^{22}=1.5290$ (compound 1).

The following compounds of formula I are prepared in accordance with the above procedure:

| Comp. No. | X | Y | R | $R_1$ | $R_2$ | $R_3$ | phys. data |
|---|---|---|---|---|---|---|---|
| 2 | S | S | —$C_2H_5$ | —$CH_3$ | —$CH_3$ | —$C_3H_7$(n) | $n_D^{21}=1.5381$ |
| 3 | S | S | —$C_2H_5$ | —$(CH_2)_4$— | | —$C_4H_9$(s) | $n_D^{20}=1.5450$ |
| 4 | S | S | —$CH_3$ | —$CH_3$ | —$CH_3$ | —$C_4H_9$(t) | $n_D^{22}=1.5379$ |
| 5 | S | S | —$CH_3$ | —$(CH_2)_4$— | | —$C_4H_9$(t) | $n_D^{22}=1.5538$ |
| 6 | S | S | —$C_2H_5$ | —$(CH_2)_4$— | | —$C_4H_9$(t) | $n_D^{22}=1.5492$ |
| 7 | S | S | —$C_2H_5$ | —$CH_3$ | —$CH_3$ | —$C_4H_9$(t) | $n_D^{22}=1.5353$ |
| 8 | O | S | —$CH_3$ | —$(CH_2)_4$— | | —$C_4H_9$(t) | $n_D^{20}=1.5077$ |
| 9 | O | S | —$CH_3$ | —$CH_3$ | —$CH_3$ | —$C_4H_9$(t) | $n_D^{20}=1.4843$ |
| 10 | S | O | —$OC_2H_5$ | —$(CH_2)_4$— | | —$C_4H_9$(s) | $n_D^{21}=1.4846$ |
| 11 | S | S | —$OC_2H_5$ | —$(CH_2)_4$— | | —$C_4H_9$(s) | $n_D^{23}=1.5262$ |
| 12 | S | S | —$OC_2H_5$ | —$CH_3$ | —$CH_3$ | —$C_4H_9$(s) | $n_D^{23}=1.5081$ |
| 13 | S | S | —$C_2H_5$ | —$CH_3$ | H | —$C_4H_9$(s) | $n_D^{23}=1.5406$ |
| 14 | S | S | —$C_2H_5$ | —$CH_3$ | H | —$C_4H_9$(t) | $n_D^{23}=1.5451$ |

The following compounds of formula I can also be obtained in accordance with the above procedure:

| X | Y | R | $R_1$ | $R_2$ | $R_3$ |
|---|---|---|---|---|---|
| S | O | $C_2H_5$ | $CH_3$ | $CH_3$ | $C_4H_9$(s) |
| S | O | $C_2H_5$ | —$(CH_2)_4$— | | $C_4H_9$(t) |
| S | S | $C_2H_5$ | $C_2H_5$ | $CH_3$ | $C_4H_9$(t) |
| S | S | $CH_3$ | $CH_3$ | $C_3H_7$(i) | $C_4H_9$(s) |

EXAMPLE 2

Formulations for active ingredients of formula I according to Example 1 (throughout, percentages are by weight)

| 1. Emulsifiable concentrates | (a) | (b) | (c) |
|---|---|---|---|
| a compound according to the Examples | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsions of any required concentration can be produced from such concentrates by dilution with water

| 2. Solutions | (a) | (b) | (c) | (d) |
|---|---|---|---|---|
| a compound according to the Examples | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3. Granulates | (a) | (b) |
| --- | --- | --- |
| a compound according to the Examples | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently removed by evaporation under vacuum.

| 4. Dusts | (a) | (b) |
| --- | --- | --- |
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers with the active ingredient.

BIOLOGICAL EXAMPLES

EXAMPLE 3

Action against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Example 1 exhibit good activity in this test.

EXAMPLE 4

Action against *Aedes aegypti*

A concentration of 400 ppm is obtained by pipetting a specific amount of a 0.1% solution of the test compound in acetone onto the surface of 150 ml of water in a beaker. After the acetone has evaporated, 30 to 40 two-day old larvae of *Aedes aegypti* are put into the beaker containing the test compound. Mortality counts are made after 2 and 7 days.

Compounds of formula I according to Example 1 exhibit good activity in this test.

EXAMPLE 5

Stomach toxicant action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

The compounds of formula I according to Example 1 exhibit good activity in this test.

EXAMPLE 6

Ovicidal action against *Laodelphax striatellus* and *Nilaparvata lugens*

The test ist carried out with growing plants. For this purpose 4 rice plants (thickness of stem 8 mm; height about 20 cm) are planted into each of a number of pots (diameter 8 cm).

The plants in each pot are sprayed on a rotary table with 100 ml of an acetonic solution containing 400 ppm of the respective test compound. After the spray coating has dried, each plant is populated with 3 adult females. To prevent the females from escaping, a glass cylinder is slipped over each of the plants and sealed with a gauze top. The females are left on the treated plant for 4 days for oviposition and are then removed.

About 8 days after the females have been placed on the plants, the young cicadas hatch from the eggs and a count is made. The percentage mortality is determined by comparing the number of larvae which have hatched on the treated plants with the number which have hatched on untreated control plants.

Compounds of formula I according to Example 1 exhibit good ovicidal activity in this test.

EXAMPLE 7

Insecticidal stomach toxicant action against *Spodoptera littoralis* and *Heliothis virescens*

Cotton plants about 25 cm high, in pots, are sprayed with aqueous emulsions which contain the test compound in a concentration of 400 ppm. After the spray coating has dried, the cotton plants are populated with *Spodoptera littoralis* and *Heliothis virescens* larvae in the $L_1$-stage. The test is carried out at 24° C. and 60% relative humidity. The percentage mortality of the test insects is determined after 120 hours by comparison with untreated controls.

In the above test, compounds 2 and 3 of Example 1 effect 80–100% kill of Heliothis and *Spodoptera larvae*. Compounds 4 to 9 effect 80–100% kill of *Spodoptera larvae*.

EXAMPLE 8

Action against *Nephotettix cincticeps* (nymphs)

The test is carried out with growing plants. For this purpose approximately twenty-day-old rice plants about 15 cm in height are planted into each of a number of pots (diameter: 5.5 cm).

The plants in each pot are sprayed on a rotary table with 100 ml of an acetonic solution containing 400 ppm of the test compound. After the spray coating has dried, each plant is populated with 20 nymphs of the test organisms in the second or third stage. To prevent the cicadas from escaping, a plexiglass cylinder is slipped over each of the plants and sealed with a gauze top. The nymphs are kept for 5 days on the treated plants, which have to be watered again at least once. The test is carried out at a temperature of about 23° C. and at 55% relative humidity. The plants are exposed to light for a period of 16 hours per day.

The compounds of formula I according to Example 1 exhibit good activity in this test.

EXAMPLE 9

Stomach toxicant and contact action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

In this test, the compounds 1, 3, 5, 6 and 8 to 12 effect 80-100% kill of *Nilaparvata lugens*.

EXAMPLE 10

Systemic action against *Nilaparvata lugens* (water)

Rice plants which are about 10 days old and about 10 cm high are put into a plastic beaker which contains 20 ml of an aqueous emulsion formulation of the test compound in a concentration of 100 ppm and which is sealed with a perforated plastic lid. The root of each rice plant is pushed through a hole in the plastic lid into the aqueous test formulation. The hole is then plugged with cotton wool to fix the plant and to exclude any contact with the gas phase of the test formulation. The rice plant is then populated with 20 nymphs of *Nilaparvata lugens* in the second to third larval stages and covered with a plastic cylinder. The test is carried out at ca. 26° C. and 60% relative humidity and the plant is exposed to a light period of 16 hours. A mortality count is made 5 days later using untreated controls for comparison purposes, thereby establishing whether the test compound absorbed through the root kills the test organisms on the upper parts of the plant.

In this test compound 3 effects 80-100% kill of *Nilaparvata lugens*.

EXAMPLE 11

Action against soil insects (*Diabrotica balteata*)

5 maize seedlings 1 to 3 cm in height and a filter paper disc are immersed in an aqueous solution containing the test compound in a concentration of 400 and 12.5 ppm. The immersed filter paper disc is placed at the bottom of a plastic beaker (capacity 200 ml). A dry filter paper disc together with the maize seedlings and 10 *Diabrotica balteata* larvae in the $L_2$- or $L_3$-stage are then placed on the first disc. The test is carried out at about 24° C. and at 40-60% relative humidity and in daylight. Evaluation is made 10 days later in comparison with untreated controls.

In this test, compounds 2 and 3 of Example 1 effect 80-100% kill at 12.5 ppm. Compounds 1, 4 to 9, 11 and 12 effect 100% kill at 400 ppm.

EXAMPLE 12

Action against *Diabrotica balteata* (in soil)

350 ml of soil (consisting of 95 vol.% of sand and 5 vol.% of peat) are mixed with 150 ml of an aqueous emulsion formulation which contains the test compound in a concentration of 0.75 ppm. Plastic beakers with a diameter of about 10 cm at the top are then partly filled with the treated soil. Ten $L_3$-larvae of *Diabrotica balteata* are put into each beaker, then 4 maize seedlings are planted and the beaker is filled with soil. The beakers are sealed with plastic sheeting and kept at about 22° C. Ten days later the soil in the beakers is sieved and a mortality count of the remaining larvae is made.

Compounds 1 to 12 of Example 1 effect 80 to 100% mortality in this test.

EXAMPLE 13

Action against *Tetranychus urticae* (OP-sensitive) and *Tetranychus cinnabarinus* (OP-tolerant)

12 hours before the test for acaricidal action, the primary leaves of *Phaseolus vulgaris* plants are infected with an infested piece of leaf from a mass culture of *Tetranychus urticae* (OP-sensitive) or *Tetranychus cinnabarinus* (OP-tolerant) (mixed population). The tolerance refers to the tolerance to diazinone. The treated infested plants are sprayed to drip point with an emulsified test solution containing the respective test compound in a concentration of 400 ppm. A count of the number of living and dead imagines and larvae (all mobile stages) is made under a stereoscopic microscope after 24 hours and again after 6 days (*T. urticae*) and after 7 days (*T. cinnabarinus*). One plant is used for each test species. During the test run, the plants are kept in greenhouse compartments at 25° C. and c. 50-60% relative humidity.

In this test, compounds of formula I according to Examples 1 exhibit good activity against *Tetranychus urticae* and *Tetranychus cinnabarinus*. Thus compounds 5, 8 and 9 effect 80-100% kill of *Tetranychus cinnabarinus*.

EXAMPLE 14

Action against parasitic mites

Batches of about 50 mites in different stages (mixed population: larvae, nymphs and adults) are taken from hens infested with *Dermanyssus gallinus*. Each batch is wetted with an aqueous emulsion, suspension or solution containing 400 ppm of test compound. This is done by pouring the liquid composition containing the test compound over the mites in a test tube. The liquid is subsequently absorbed by cotton wool. The wetted and treated mites remain in the test tube for 72 hours, after which time the mortality of the treated mites is determined in comparison with untreated controls.

The compounds of Example 1 exhibit good activity in this test.

EXAMPLE 15

Action against *Lucilia sericata*

1 ml of an aqueous formulation containing 0.1% per weight of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of formula I according to Example 1 exhibit good activity against *Lucilia sericata*.

EXAMPLE 16

Contact action against *Aphis craccivora*

Before the start of the test, 4- to 5-day old bean seedlings (*Vicia faba*) reared in pots are each populated with about 200 insects of the species *Aphis craccivora*. The treated plants are sprayed direct to drip point 24 hours later with an aqueous formulation containing 400 ppm of the test compound. Two plants are used for each test compound at the given concentration. A mortality count is made after 24 and 72 hours respectively. The test is carried out at 21°–22° C. and at a relative humidity of about 55%.

In this test, compounds 5 to 9 of Example 1 effect 80–100% kill.

EXAMPLE 17

Ovicidal action against *Heliothis virescens*

Corresponding amounts of a wettable powder formulation containing 25% by weight of the test compound are mixed with sufficient water to produce an aqueous emulsion with an active ingredient concentration of 400 ppm. One-day-old egg deposits of Heliothis on cellophane ® are immersed in these emulsions for 3 minutes and then collected by suction on round filters. The treated deposits are placed in petri dishes and kept in the dark. The hatching rate is determined after 6 to 8 days in comparison with untreated controls.

In this test, compounds 1, 2, 4 to 7 and 8 effect 80 to 100% kill.

EXAMPLE 19

Action against ticks

Adult females of the cattle tick, *Boophilus microplus*, which are replete with blood, are used as test organisms. Ten ticks of an OP-sensitive strain (e.g. Biarra strain) and 10 ticks of a normally sensitive strain (e.g. Yeerongpilly strain) are treated. The ticks are affixed to plates to which double-sided adhesive tape has been applied and are then covered for 1 hour with a cotton wool swab impregnated with an aqueous emulsion or solution containing 400 ppm of the test compound. After removing the cotton wool swab, the ticks are dried overnight at 24° C. and then kept in a controlled environment chamber under constant conditions (28° C., 80% relative humidity) for 4 weeks until the completion of oviposition and the start of larval hatching. Evaluation is made by determining mortality as well as the percentage inhibition of fertile eggs (blockage of embryogenesis or inhibition of hatching) in comparison with untreated controls.

The compounds of formula I according to Example 1 exhibit good activity in this test.

EXAMPLE 19

Action against ticks: Killing action in various development stages

About 50 larvae, about 25 nymphs or about 10 imagines of each of the tick species *Rhipicephalus bursa, Amblyomma hebraeum* and *Boophilus microplus* are used as test organisms. The test organisms are immersed for a short time in aqueous emulsions containing the respective test compound in a concentration of 800 ppm. The emulsions, which are contained in test tubes, are then absorbed by cotton wool, and the wetted test organisms are left in the test tubes which have thus been contaminated. Evaluation of the percentage mortality is made 3 days later in the case of the larvae and 14 days later in the case of the nymphs and imagines.

Compounds of formula I according to Example 1 exhibit good activity in this test.

What is claimed is:

1. A compound of formula I $$\begin{array}{c} X \quad Y-R_3 \\ \| / \\ R-P \quad OR_1 \\ \diagdown N \diagup \\ | \\ R_2 \end{array} \quad (I)$$

wherein:

R is $C_1$–$C_4$alkyl, $R_1$ and $R_2$ are each methyl or, when taken together, form the radical —$(CH_2)_4$—, $R_3$ is $C_3$–$C_4$alkyl;

X is oxygen or sulfur, and

Y is sulfur.

2. A compound of formula I according to claim 1, wherein R is methyl or ethyl.

3. A compound of formula I according to claim 1, wherein X and Y are sulfur.

4. A compound of formula I according to claim 1, wherein $R_3$ is n-propyl, isopropyl, sec-butyl or tert-butyl.

5. A compound according to claim 1 of formula $$\begin{array}{c} S \quad S-C_3H_7(n) \\ \| / \\ C_2H_5-P \quad O-CH_3 \\ \diagdown N \diagup \\ | \\ CH_3 \end{array}$$

6. A compound according to claim 1 of formula $$\begin{array}{c} S \quad S-C_4H_9(s) \\ \| / \\ C_2H_5-P \quad O \\ \diagdown N \diagup \\ | \end{array}$$

7. A compound according to claim 1 of formula

8. A compound according to claim 1 of formula

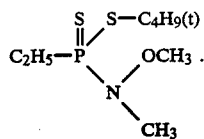

9. A compound according to claim 1 of formula

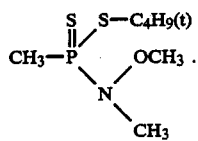

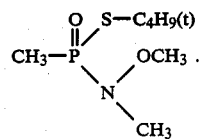

10. A pesticidal composition which contains an effective amount of a compound as claimed in claim 1 as active component, together with suitable carriers and/or other adjuvants.

11. A method of controlling insects and representatives of the order Acarina, which comprises contacting or treating said pests or the different development stages thereof and/or the locus thereof with a pesticidally effective amount of a compound of formula I as claimed in claim 1, or with a composition which contains a pesticidally effective amount of such a compound, together with adjuvants and carriers.

12. The method of claim 11, wherein the pests to be controlled are insects and representatives of the order Acarina that are parasites of animals and plants.

13. The method of claim 11, wherein the pests to be controlled are plant-destructive insects.

14. The method of claim 13, wherein the pests to be controlled are larval stages of plant-destructive insects.

15. The method of claim 11, wherein the pests to be controlled are ticks and mites that are parasites of domestic animals and productive live-stock.

* * * * *